(12) United States Patent
Lloyd et al.

(10) Patent No.: US 6,586,640 B2
(45) Date of Patent: Jul. 1, 2003

(54) DECOMPOSITION OF ORGANIC HYDROPEROXIDES IN THE PRESENCE OF A PARTICULATE CATALYST CONTAINING HIGHLY FLUORINATED POLYMER HAVING SULFONIC ACID GROUPS AND PROCESS FOR THE MANUFACTURE OF BISPHENOL A

(75) Inventors: Ralph Birchard Lloyd, Fayetteville, NC (US); Qun Sun, Wilmington, DE (US); Mark Andrew Harmer, Kennett Square, PA (US); Edward George Howard, Jr., Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/177,853

(22) Filed: Jun. 20, 2002

(65) Prior Publication Data

US 2003/0050513 A1 Mar. 13, 2003

Related U.S. Application Data

(60) Provisional application No. 60/300,840, filed on Jun. 26, 2001.

(51) Int. Cl.$^7$ ................................................. C07C 37/08
(52) U.S. Cl. ....................... 568/798; 568/385; 568/727; 568/728; 568/768
(58) Field of Search ................................ 568/798, 768, 568/385, 727, 728

(56) References Cited

U.S. PATENT DOCUMENTS

| | | | |
|---|---|---|---|
| 3,282,875 A | | 11/1966 | Connolly et al. |
| 4,053,522 A | * | 10/1977 | McClure |
| 4,322,560 A | | 3/1982 | Vaughan |
| 4,339,613 A | * | 7/1982 | Olah |
| 4,339,614 A | * | 7/1982 | Olah |
| 4,358,545 A | | 11/1982 | Ezzell et al. |
| 4,433,082 A | | 2/1984 | Grot |
| 4,940,525 A | | 7/1990 | Ezzell et al. |
| 6,281,400 B1 | * | 8/2001 | Harmer |

FOREIGN PATENT DOCUMENTS

| | | |
|---|---|---|
| JP | 62221650 | 9/1987 |
| WO | WO 96/19288 | 6/1996 |
| WO | WO 99/06145 | 2/1999 |

* cited by examiner

*Primary Examiner*—Michael L. Shippen

(57) ABSTRACT

A process for the manufacture of a hydroxy-substituted organic compound comprising decomposing an organic hydroperoxide, preferably a compound of the formula Ar—C(CH$_3$)$_2$O$_2$H, wherein Ar is a substituted or unsubstituted mononuclear or polynuclear aromatic group. The decomposition is carried out in the presence of a catalyst comprising highly fluorinated polymer having sulfonic acid groups with the catalyst being in the form of particles of which at least about 20 weight % have a particle size less than about 300 µm. Cumene hydroperoxide can be decomposed in the process to phenol and acetone which can be reacted to form bisphenol A in the presence of the same catalyst that was used for the decomposition.

16 Claims, No Drawings

DECOMPOSITION OF ORGANIC HYDROPEROXIDES IN THE PRESENCE OF A PARTICULATE CATALYST CONTAINING HIGHLY FLUORINATED POLYMER HAVING SULFONIC ACID GROUPS AND PROCESS FOR THE MANUFACTURE OF BISPHENOL A

FIELD OF THE INVENTION

The present invention relates to the decomposition of organic hydroperoxides to hydroxy-substituted organic compounds and carbonyl compounds in the presence of a particulate catalyst containing highly fluorinated polymer having sulfonic acid groups.

BACKGROUND OF THE INVENTION

Commercial processes for the manufacture of hydroxy-substituted organic compounds, particularly aromatic compounds such as phenol and hydroquinone, often employ reaction routes that require the decomposition of organic hydroperoxides. For example, phenol is manufactured from cumene by converting it to the hydroperoxide followed by decomposition to phenol and acetone. The hydroperoxide decomposition reaction is an acid-catalyzed reaction and a concentrated sulfuric acid solution at temperatures in the range of 50–100° C. is typically employed in commercial processes.

Though it provides effective catalysis, the use of sulfuric acid for the cumene hydroperoxide decomposition reaction has disadvantages. Since it is a homogenous catalyst, it is necessary to employ one or more process steps to separate it from the product mixture. The spent sulfuric acid must be neutralized and disposed of. Moreover, using sulfuric acid causes the product mixture to contain significant percentages of undesirable side products which reduce yields and require additional process steps for removal.

U.S. Pat. No. 4,322,560 discloses using a thin film of solid acid catalyst of perfluorocarbon polymer containing pendant sulfonic acid groups for the decomposition of organic hydroperoxides. However, the reaction rate is not sufficiently high at desirable process temperatures for the process to be particularly useful commercially. PCT Publication No. WO 96/19288, published Jun. 27, 1996, discloses catalysts which comprise porous microcomposites of perfluorinated ion exchange polymer and a metal oxide network. Numerous reactions are disclosed in this publication including the decomposition of organic hydroperoxides. While decomposition results using catalysts disclosed in this publication, the reaction rate again is not sufficiently high at desirable process temperatures to be particularly useful commercially.

SUMMARY OF THE INVENTION

The invention provides a process for the manufacture of a hydroxy-substituted organic compound comprising decomposing an organic hydroperoxide in the presence of a catalyst containing highly fluorinated polymer having sulfonic acid groups, the catalyst being in the form of particles of which at least about 20 weight % have a particle size less than about 300 $\mu$m. In a preferred form of the invention, the catalyst is selected from the group consisting of (a) particles of highly fluorinated polymer having sulfonic acid groups and (b) particles of porous microcomposite of a metal oxide network and highly fluorinated polymer having sulfonic acid groups. Preferably, the process provides for the manufacture of a hydroxy-substituted aromatic compound comprising by the decomposition of a compound of the formula Ar—C(CH$_3$)$_2$O$_2$H, wherein Ar is a substituted or unsubstituted mononuclear or polynuclear aromatic group.

It has been discovered that a process employing catalyst particles having a particle size in accordance with the present invention increases the rate of the decomposition reaction and can provide higher reaction rates than in existing processes. In addition, hydroxy-substituted organic compounds are produced in high yield at moderate temperatures and in higher purity, i.e., with fewer undesirable side products than in existing commercial processes.

The invention also provides a process for the manufacture of 2,2-Bis(4-hydroxyphenyl)-propane (hereinafter referred to as Bisphenol A). The process includes:

(a) decomposing cumene hydroperoxide in the presence of a catalyst containing highly fluorinated polymer having sulfonic acid groups to form a decomposition product mixture containing phenol and acetone; and (b) reacting the phenol and acetone of the decomposition product mixture in the presence of catalyst containing highly fluorinated polymer having sulfonic acid groups under conditions which promote the formation bisphenol A.

In a preferred embodiment of the process, at least a portion of the phenol and acetone of the decomposition product mixture is not separated from the catalyst prior to the reaction to form bisphenol A and the catalyst used for the decomposition is the same catalyst that is used for the reaction to bisphenol A.

DETAILED DESCRIPTION

The catalyst employed in accordance with the present invention contains highly fluorinated polymer having sulfonic acid groups. "Highly fluorinated" means that at least 90% of the total number of univalent atoms in the polymer are fluorine atoms. Most preferably, the polymer is perfluorinated.

Preferably, the polymer of the catalyst comprises a polymer backbone with recurring side chains attached to the backbone, the side chains carrying the sulfonic acid groups. Possible polymers include homopolymers or copolymers of two or more monomers. Copolymers are typically formed from one monomer which is a nonfunctional monomer and which provides carbon atoms for the polymer backbone. A second monomer provides carbon atoms for the polymer backbone and also contributes the side chain carrying the sulfonic acid group or its precursor, e.g., a sulfonyl halide group such a sulfonyl fluoride (—SO$_2$F), which can be subsequently hydrolyzed to a sulfonic acid functional group. For example, copolymers of a first fluorinated vinyl monomer together with a second fluorinated vinyl monomer having a sulfonyl fluoride group (—SO$_2$F) can be used. Possible first monomers include tetrafluoroethylene (TFE), hexafluoropropylene, vinyl fluoride, vinylidine fluoride, trifluoroethylene, chlorotrifluoroethylene, perfluoro (alkyl vinyl ether), and mixtures thereof. Possible second monomers include a variety of fluorinated vinyl ethers with sulfonic acid functional groups or precursor groups which can provide the desired side chain in the polymer. Additional monomers can also be incorporated into these polymers if desired. TFE is a preferred monomer.

A class of preferred polymers for use in the present invention include a highly fluorinated, most preferably perfluorinated, carbon backbone and the side chain is represented by the formula —(O—CF$_2$CFR$_f$)$_a$—O—

$CF_2CFR'_fSO_3H$, wherein $R_f$ and $R'_f$ are independently selected from F, Cl or a perfluorinated alkyl group having 1 to 10 carbon atoms, and a=0, 1 or 2. The preferred polymers include, for example, polymers disclosed in U.S. Pat. No. 3,282,875 and in U.S. Pat. Nos. 4,358,545 and 4,940,525. One preferred polymer comprises a perfluorocarbon backbone and the side chain is represented by the formula —O—$CF_2CF(CF_3)$—O—$CF_2CF_2SO_3H$. Polymers of this type are disclosed in U.S. Pat. No. 3,282,875 and can be made by copolymerization of tetrafluoroethylene (TFE) and the perfluorinated vinyl ether $CF_2$=CF—O—$CF_2CF(CF_3)$—O—$CF_2CF_2SO_2F$, perfluoro(3,6-dioxa-4-methyl-7-octenesulfonyl fluoride) (PDMOF), followed by hydrolysis of the sulfonyl halide groups to sulfonate groups, and acid exchange to convert the sulfonate groups to the proton form. One preferred polymer of the type disclosed in U.S. Pat. Nos. 4,358,545 and 4,940,525 has the side chain —O—$CF_2CF_2SO_3H$. This polymer can be made by copolymerization of tetrafluoroethylene (TFE) and the perfluorinated vinyl ether $CF_2$=CF—O—$CF_2CF_2SO_2F$, perfluoro (3-oxa-4-pentenesulfonyl fluoride) (POPF), followed by hydrolysis and acid exchange.

In this application, "ion exchange ratio" or "IXR" is defined as the number of carbon atoms in the polymer backbone in relation to the cation exchange groups. A wide range of IXR values for the polymer are possible. Typically, however, the IXR range used for the catalyst is usually about 7 to about 33. For perfluorinated polymers of the type described above, the cation exchange capacity of a polymer is often expressed in terms of equivalent weight (EW). For the purposes of this application, equivalent weight (EW) is defined to be the weight of the polymer in acid form required to neutralize one equivalent of NaOH. In the case of a sulfonic acid polymer in which the polymer comprises a perfluorocarbon backbone and the side chain is —$CF_2$—CF($CF_3$)—O—$CF_2$—$CF_2$—$SO_3H$, the equivalent weight range which corresponds to an IXR of about 7 to about 33 is about 700 EW to about 2000 EW. IXR for this polymer can be related to equivalent weight using the following formula: 50 IXR+344=EW. While generally the same IXR range is used for sulfonic acid polymers disclosed in U.S. Pat. Nos. 4,358,545 and 4,940,525, the equivalent weight is somewhat lower because of the lower molecular weight of the monomer unit containing the sulfonic acid group. For the IXR range of about 7 to about 33, the corresponding equivalent weight range is about 500 EW to about 1800 EW. IXR for this polymer can be related to equivalent weight using the following formula: 50 IXR+178=EW.

IXR is used in this application to describe either hydrolyzed polymer which contains functional groups or unhydrolyzed polymer which contains precursor groups which will subsequently be converted to the functional groups during the manufacture of the catalyst.

The highly fluorinated polymer having sulfonic acid groups used in the process of the invention preferably has ion exchange ratio of about 8 to about 23, more preferably about 9 to about 14 and most preferably about 10 to about 13.

Other ion exchange groups such as carboxylic acid groups may be present in the highly fluorinated polymer provided that a sufficient quantity of sulfonic acid groups are present in the polymer for the catalyst to provide a suitably high reaction rate for a commercial process. In addition, the polymer may be partially cation-exchanged with some of the sulfonic acid groups present in cation-exchanged form, i.e., sodium, potassium, etc., provided that a sufficient quantity of sulfonic acid groups are retained. Preferably, the polymer contains only sulfonic acid groups and is at least about 80% acid exchanged, more preferably, at least about 90% acid exchanged, still more preferably at least about 98% acid exchanged, and most preferably substantially completely acid exchanged.

It has been discovered that use of catalyst particles in a specified size range, disclosed below, increases the rate of the decomposition reaction dramatically. Particle size is the number average particle size, and is measured by optical and electron microscopy. The particles of catalyst used in a process in accordance with the invention can have any of a variety of shapes and may be highly irregular. When particles have an aspect ratio, particle size refers to the longest dimension of the particles. By having an aspect ratio is meant that the particles are not round or spherical.

In the process according to the invention, the catalyst may contain some larger catalyst particles provided that a sufficient quantity particles of the specified size are present to achieve the desired result. However, larger particles will reduce the effectiveness of the catalyst per unit of weight and it is preferred that substantial quantities of larger particles to be excluded. Therefore, at least about 20 weight % of the catalyst, preferably at least about 30 weight % of the catalyst, more preferably at least about 40 weight % of the catalyst, still more preferably at least about 65 weight % of the catalyst, still more preferably at least about 80 weight %, still more preferably at least about 90 weight %, and most preferably substantially all of the catalyst has a particle size less than about 300 $\mu$m. It is further preferable for the above-stated weight percentages of the catalyst to have a particle size less than about 100 $\mu$m. The minimum particle size for the catalyst is preferably greater than about 0.02 $\mu$m, more preferably greater than about 0.05 $\mu$m, most preferably greater than about 0.1 $\mu$m.

Preferably, the particles are in a size range which enables them to be separated from the product mechanically using techniques typically used for heterogeneous catalysts in liquid systems. If desired, a fixed bed of the catalyst can be used.

For the practice of the present invention, it is preferred that the catalyst be in the form of particles of the polymer itself, i.e., highly fluorinated polymer having sulfonic acid groups, or in the form of particles of porous microcomposite of a metal oxide network and highly fluorinated polymer having sulfonic acid groups. Porous microcomposites which are useful in the practice of the invention are described in PCT Publication No. WO 96/19288, published Jun. 27, 1996. The porous microcomposites disclosed comprise a perfluorinated ion-exchange polymer entrapped within and highly dispersed throughout a network of metal oxide. The weight percentage of perfluorinated ion-exchange polymer in the microcomposite is from about 0.1 to 90 percent, preferably from about 5 to about 80 percent, and most preferably about 5 to about 25 percent. The size of the pores in the microcomposite is about 0.5 nm to about 75 nm and, optionally, further comprises pores having a size in the range of about 75 nm to about 1000 nm.

The microcomposites described in PCT Publication No. WO 96/19288 exist as particulate solids which are porous and glass-like in nature and are structurally hard, similar to dried silica gels. The porous nature of the microcomposites is evident from their high surface areas.

"Metal oxide" signifies metallic or semimetallic oxide compounds, including, for example, alumina, silica, titania, germania, zirconia, alumino-silicates, zirconyl-silicates, chromic oxides, germanium oxides, copper oxides, molybdenum oxides, tantalum oxides, zinc oxides, yttrium oxides, vanadium oxides, and iron oxides. Preferably, the network of metal oxide of the microcomposite is selected from the group consisting of: silica, alumina, titania, germania, zirconia, alumino-silicate, zirconyl-silicate, chromic oxide and iron oxide. Silica is the most preferred metal oxide.

A process for manufacture of the microcomposites is disclosed in PCT Publication No. WO 96/19288 and employs a metal oxide precursor which is employed in a sol-gel process to produce a metal oxide in the microcomposite. This process is useful in the manufacture catalysts for the practice of the present invention provided that the size of the composite particles is reduced as described hereinafter.

Catalyst particles of a size suitable for the present invention may be formed by mechanically grinding (a) highly fluorinated polymer having sulfonic acid groups or (b) porous microcomposites of metal oxide and highly fluorinated polymer having sulfonic acid groups. For grinding the polymer itself, particle size in the desired range can be suitably accomplished by cryogrinding. Size reduction of the porous microcomposites can be suitably accomplished by grinding at room temperature. The resulting particles can be sieved or otherwise treated if necessary to separate particles that are less than about 300 μm, and preferably less than about 100 μm, for use in the process of the invention.

Alternatively, suitable catalyst can be produced by spray drying a liquid, preferably aqueous, dispersion of highly fluorinated polymer having sulfonic acid groups and/or such a dispersion also containing metal oxide precursor. Spray drying using a commercial spray drier such as that produced by Niro, of Columbia, Md., can produce particles typically in the range of about 0.5 μm to about 50 μm.

The process in accordance with the invention produces hydroxy-substituted organic compounds by decomposing organic hydroperoxide. The process is especially useful in the manufacture of a hydroxy-substituted aromatic compound comprising decomposing a compound of the formula Ar—C(CH$_3$)$_2$O$_2$H, wherein Ar is a substituted or unsubstituted mononuclear or polynuclear aromatic group. Two preferred reactions are (1) the decomposition of cumene hydroperoxide and (2) the decomposition of diisopropylbenzene dihydroperoxide.

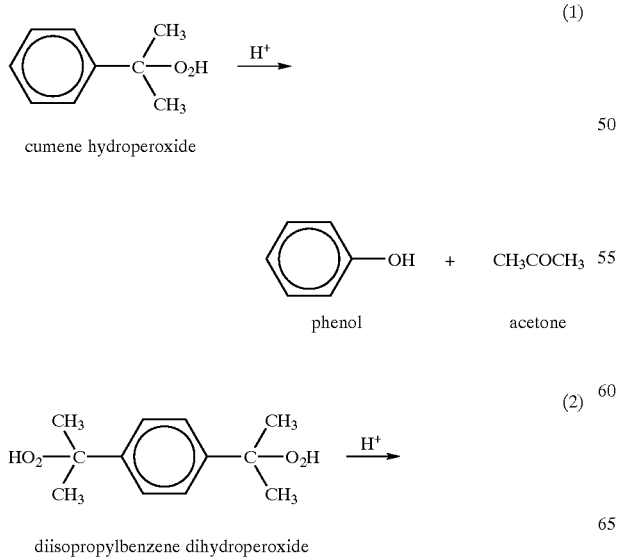

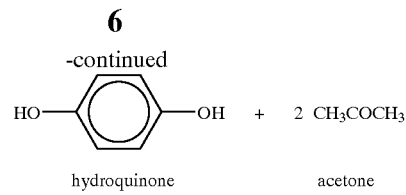

The process is preferably carried out in organic solvents such as acetone, dichlorobenzene, benzene, or chloroform. In the preferred forms of the invention, the decomposition of cumene hydroperoxide and the decomposition of diisopropylbenzene dihydroperoxide in which acetone is a reaction product, a preferred organic solvent is acetone.

Preferably, the temperature of the reaction is about −15° C. to about 150° C., and most preferably about 20° C. to about 100° C. If the chosen reaction temperature is above the boiling point of the solvent at atmospheric pressure, the reaction can be carried out in a pressure vessel.

The highly fluorinated polymer having sulfonic acid catalyst of small particle size described herein before or of larger particle size, is also useful for the manufacture of 2,2-Bis (4-hydroxyphenyl)-propane (Bisphenol A). In this reaction, cumene hydroperoxide is decomposed in the presence of catalyst containing highly fluorinated polymer containing sulfonic acid groups to form a decomposition product mixture containing phenol and acetone. The phenol and acetone from the decomposition product mixture is reacted in the presence of the fluoropolymer sulfonic acid catalyst under conditions which form bisphenol A. Preferably, at least a portion of the phenol and acetone of the decomposition product mixture is not separated from the catalyst prior to the reaction to form bisphenol A and the catalyst used for the decomposition is the same catalyst that is used for the reaction to bisphenol A. The reaction to make bisphenol A proceeds at reasonable rates at the same temperatures as the hydroperoxide decomposition. Preferably, the mole ratio of phenol relative to acetone is increased prior to reaction to form bisphenol A, and such increase is preferably achieved by removing some acetone from the decomposition product mixture. The catalyst present during the decomposition of cumene hydroperoxide and in the phenol/acetone reaction is preferably in the form of particles wherein at least about 20 weight % of the catalyst, more preferably at least about 30 weight % of the catalyst, still more preferably at least about 40 weight % of the catalyst, still more preferably at least about 65 weight % of the catalyst, still more preferably at least about 80 weight %, still more preferably at least about 90 weight %, and most preferably substantially all of the catalyst has a particle size less than about 300 μm. It is further preferable for the above-stated weight percentages of the catalyst to have a particle size less than about 100 μm. The minimum particle size for the catalyst is preferably greater than about 0.02 μm, more preferably greater than about 0.05 μm, most preferably greater than about 0.1 μm.

EXAMPLES

In the examples which follow, the perfluorinated sulfonic acid polymer (PFSAP) is a copolymer of TFE and PDMOF and has an equivalent weight of approximately 1070. Unless otherwise indicated, "solutions" are dispersions of the same polymer in a medium of approximately 45 weight % water, 22 weight % 1-propanol, 22 weight % 2-propanol, 3 weight % methanol and 3 weight % of mixed ethers and other volatile organic compounds made using the procedure described in U.S. Pat. No. 4,433,082. The balance is polymer. Solutions of this type are commercially available from E.I. du Pont de Nemours and Company, Wilmington, Del.

Example 1

Preparation of a 13 Weight % Perfluorinated Sulfonic Acid Polymer/87 Weight % Silica Microcomposite (SAC-13a)

240 g of tetraethylorthosilicate ($Si(OEt)_4$), 69 g of distilled water and 1.15 g of 3.5 M HCl are stirred for 2 hours to give a clear solution, designated Solution A. To 240 ml of a perfluorinated sulfonic acid polymer solution (5 weight % perfluorinated sulfonic acid polymer) is added to 120 ml of 0.4 M NaOH at once, while the solution is stirred. Solution A is then added rapidly to the stirred perfluorinated sulfonic acid polymer containing solution. After a few seconds the whole system gels. The gel is dried by placing it in an oven at a temperature of about 95–100° C. for a period of about 2 days. The hard glass-like product is ground and passed through a 10-mesh screen. The solid is then treated with 2 liters of 25 weight % nitric acid and the mixture is gently stirred for 12 hours and the acid is decanted and then replaced with deionized water (2 liters) and stirred for a further 12 hours. The solid is filtered and resuspended in 2 liters of 25 weight % nitric for an additional 12 hours followed by treating with deionized water (2 liters, stirred for 12 hours). This process is repeated for a third time (acid and water treating) and the material is filtered and then dried further at 110° C. under vacuum overnight. The solid (about 80 g) contains about 13 weight % of the perfluorinated sulfonic acid polymer as can be determined by thermogravimetric analysis (the polymer loading can be determined by heating the solid up to 800° C. and measuring the weight loss between 400–600° C.). Particle size is about 1000–3000 µm.

Example 2

Preparation of a 13 Weight % Perfluorinated Sulfonic Acid Polymer/87 Weight % Silica Microcomposite (SAC-13b)

This example uses perfluorinated sulfonic acid polymer solution that is essentially an aqueous solution. The is prepared by taking a 5 weight % perfluorinated sulfonic acid polymer solution, and removing the alcohol by distillation to give 12 weight % aqueous solution. To 25 g of the 12 weight % aqueous perfluorinated sulfonic acid polymer solution, additional water is added to bring the total weight to 100 g. This gives a perfluorinated sulfonic acid polymer concentration of about 3 weight %. A 10 weight % sodium silicate solution is made by adding 70 g of sodium silicate (with about 29 weight % silica) to 200 g water. The perfluorinated sulfonic acid polymer solution is added to the sodium silicate solution while stirring for about 2 minutes. Then, stirring is continued for about another 5 minutes. To this 52 g of 3.5 M HCl is added giving a pH in the range of 7–7.5. The system gels in about 5–10 seconds. The gel is dried by placing it in an oven at a temperature of about 95–100° C. for a period of about 2 days. The hard glass-like product is ground and passed through a 10-mesh screen. The solid is then treated by treating with 2 liters of 25 weight % nitric acid and the mixture is gently stirred for 12 hours. The acid is decanted and then replaced with deionized water (2 liters) and stirred for another 12 hours. The solid is filtered and resuspended in 2 liters of 25 weight % nitric acid for a further 12 hours followed by treating with water (2 liters, stirred for 12 hours). This process is repeated for a third time (acid and water treating) and the material is filtered and then dried at 110° C. under vacuum overnight. The solid (about 25 g) contains about 13 weight % of the perfluorinated sulfonic acid polymer as can be determined by thermogravimetric analysis (the polymer loading can be determined by heating the solid up to 800° C. and measuring the weight loss between 400–600° C.). Particle size is about 1–3 mm.

Example 3

Preparation of a Reduced Particle Size 13 Weight % Perfluorinated Sulfonic Acid Polymer/87 Weight % Silica Microcomposite (Ground SAC -13b)

20 g of solid is prepared as described in Example 2 and is further subjected to grinding in a mechanical mortar and pestle (FRITSCH PULVERISETLE AUTOGRINDER) for about 1 hour. Using a scanning electron microscope, the particle size is determined to be in the range of 0.2 to 20 µm.

Example 4

Preparation of a Reduced Particle Size 80 Weight % Perfluorinated Sulfonic Acid Polymer/20 Weight % Silica Microcomposite (Ground SAC-80)

To 1680 ml of a perfluorinated sulfonic acid polymer solution (which contains 5 weight % perfluorinated sulfonic acid polymer) is added 140 ml of 0.4 M NaOH at once, while the solution is being stirred. 56 g of $Si(OMe)_4$ is added to 9.8 g of water and 0.8 g of 0.04 M HCl and the mixture is stirred for one hour. The silicon containing solution is added rapidly to the stirred perfluorinated sulfonic acid polymer containing solution. The system gels and the gel is dried by placing it in an oven at a temperature of about 95–100° C. for a period of about 2 days. The hard glass-like product is subjected to grinding with a mechanical mortar and pestle for about 1 hour. Using a scanning electron microscope the particle size is determined to be in the range of 0.2 to 20 microns in size. The solid is then treated with 2 liters of 25 weight % nitric acid and the mixture is gently stirred for 12 hours. The acid is decanted and then replaced with deionized water (2 liters) and stirred for a further 12 hours. The solid is filtered and resuspended in 2 liters of 25 weight % nitric for another 12 hours followed by treating with water (2 liters, stirred for 12 hours). This process is repeated for a third time (acid and water treating) and the material is filtered and then dried at 110° C. overnight under vacuum. The solid (about 25 g) contains about 80 weight % of the perfluorinated sulfonic acid polymer as can be determined by thermogravimetric analysis (the polymer loading can be determined by heating the solid up to 800° C. and measuring the weight loss between 400–600° C.). Particle size is in the range of 0.2 to 20 µm.

Example 5

Preparation of Reduced Particle Size 100% Perfluorinated Sulfonic Acid Polymer (Ground PFSAP) Resin by Cryogenic Grinding

Part A

Perfluorinated sulfonic acid polymer pellets and liquid nitrogen are introduced into a Bantam Micropulverizer. Grinding is carried out at liquid nitrogen temperature, at 1400 rpm and with a screen size of 0.125 inch (0.32 cm) and are ground for a period of approximately five minutes to produce a powder. The powder is sieved through standard test sieves and particles with a size of 250–300 µm (50–60 mesh) are collected.

Part B

The powder of Part A is sieved through a 270 mesh screen and particles with a size of less than 50 µm are collected.

Example 6

Preparation of Reduced Particle Size 100% Perfluorinated Sulfonic Acid Polymer (Spray-Dried PFSAP) Resin by Spray Drying

100 g of the 12 weight percent water-only perfluorinated sulfonic acid polymer solution as made in Example 2 is spray dried using a commercial spray dryer sold by Niro of Columbia, Md., with an inlet temperature of 300° C. and an outlet temperature of 160° C. The powder is washed by stirring with 2 liters of 25 weight % nitric acid heated to 70° C. The solid is filtered and the washing process is repeated once. The particle size of the spray dried material is determined to be in the range of 0.5 to 15 μm.

Example 7

Preparation of a Reduced Particle Size 90 Weight % Perfluorinated Sulfonic Acid Polymer/10 Weight % Silica Microcomposite (Spray Dried SAC-90)

280 g of sodium silicate solution (about 29 weight % silica) is added to 800 g of water. The sodium silicate solution is slowly added to 488 g of Dowex cation exchange resin in 100 g of water. The pH is kept between 2.5 to 3 via the slow addition (over 1–2 hours) of the silicate solution. 1042 g of a 12 weight % containing perfluorinated sulfonic acid polymer solution (perfluorinated sulfonic acid polymer in water is added to 180 g of the ~7 weight % silica containing solution. The solution is spray dried using a commercial spray dryer sold by Niro of Columbia, Md., with an inlet temperature of 300° C. and an outlet temperature of 160° C. The powder is washed by stirring with 2 liters of 25 weight % nitric acid heated to 70° C. The solid is filtered and the washing process is repeated once. The particle size of the spray dried material is determined to be in the range of 0.5 to 15 μm.

Example 8

Decomposition of Cumene Hydroperoxide

The process of the present invention is compared to processes using sulfuric acid and to perfluorinated sulfonic acid polymer catalysts of larger particle sizes. The acid catalysts employed in the procedure described below for the peroxide decomposition include sulfuric acid, perfluorinated sulfonic acid polymer resin pellet, 13 weight % perfluorinated sulfonic acid polymer/silica microcomposites (SAC-13A, SAC-13B, ground SAC-13B), 80% perfluorinated sulfonic acid polymer/silica microcomposite (ground SAC-80), 100% perfluorinated sulfonic acid polymer powders from cryogenic grinding (ground PFSAP) and from spray drying, and 90% perfluorinated sulfonic acid polymer/silica microcomposite from spray drying. Particle size for the catalysts is listed in Table 1.

For each catalyst, five 3 ml vials are used as follows. To each 3 ml vial is added 2 ml acetone, 1–20 mg catalyst and a magnetic stir bar. The vial is sealed with a cap that has a PTFE/silicone septum. Then it is heated and stirred with Heating/Stirring Module (Pierce Reacti-Therm). At the reaction temperature, 50° C., 50–80 microliter cumene hydroperoxide is added with a syringe through the septum. (The cumene hydroperoxide which is used is 80 weight % and available from Aldrich Chemical Co. Milwaukee Wis. USA. GC/MS analysis indicates the main impurities are cumene, 2-phenyl-2-propanol and acetophenone.) At 2, 5, 15, 30 and 60 minute intervals, one of the vials for each catalyst is removed from the module and quenched in a 0° C. ice water bath. The reaction mixture is quickly filtered to remove solid acid catalyst. In the case of $H_2SO_4$ catalyzed reaction, it is quenched by aqueous $NaHCO_3$ solution. The reaction mixtures of each of the vials are analyzed by a Hewlett-Packard 5890 series II gas chromatography that is equipped with a flame ionization detector (FID).

Table 1 lists the reaction rates for the processes being compared. Typically, quantitative yield of phenol can be obtained given enough reaction time. In the case of $H_2SO_4$, the reaction mixture becomes noticeably dark after the reaction, indicating tar formation. The reaction mixtures using perfluorinated sulfonic acid polymer catalysts do not darken in any of the reactions. In three instances, Ground SAC-80, Spray-dried PFSAP and Spray-dried SAC-90, the reaction rate could not be determined with certainty where the reactions go to completion within 2 minutes at 50° C. with the peroxide/catalyst ratio=80 μl/2 mg. Rates for these reactions are estimated to be >10,000 mM/gcat·.h.

Data in Table 1 clearly show that the process in accordance with the invention with a catalyst containing highly fluorinated polymer with sulfonic acid groups and having a particle size of less than about 300 μm produces at least an order of magnitude increase in rate compared to using of standard catalysts. Reaction rates using perfluorinated sulfonic acid polymer catalyst powders can be more than 100 times higher than the PFSAP pellets.

TABLE 1

Reaction Rate for the Acid Catalyzed Decomposition of Cumene Hydroperoxide in Acetone at 50° C.

| Catalyst | Particle Size | Rate (mM/gcat.h) |
|---|---|---|
| $H_2SO_4$ | — | 780 |
| PFSAP Resin (Pellet) | 3–5 mm | 110 |
| SAC-13A (Example 1) | 1–3 mm | 120 |
| SAC-13B (Example 2) | 1–3 mm | 210 |
| Ground SAC-13B (Example 3) | 0.2–20 μm | 1,560 |
| Ground SAC-80 (Example 4) | 0.2–20 μm | >10,000 |
| Ground PFSAP Resin (Example 5, Part A) | 250–300 μm | 1150 |
| Ground PFSAP Resin (Example 5, Part B) | <50 μm | 11,200 |
| Spray-dried PFSAP Resin (Example 6) | <50 μm | >10,000 |
| Spray-dried SAC-90 (Example 7) | 0.5–15 μm | >10,000 |

What is claimed is:

1. A process for the manufacture of a hydroxy-substituted organic compound comprising decomposing an organic hydroperoxide in the presence of a catalyst containing highly fluorinated polymer having sulfonic acid groups, said catalyst being in the form of particles of which at least about 20 weight % have a particle size less than about 300 μm.

2. The process of claim 1 wherein said catalyst is selected from the group consisting of
   (a) particles of highly fluorinated polymer having sulfonic acid groups and
   (b) particles of porous microcomposite of a metal oxide network and highly fluorinated polymer having sulfonic acid groups.

3. The process of claim 1 wherein said catalyst is selected from the group consisting of
  (a) particles of highly fluorinated polymer having sulfonic acid groups and
  (b) particles of porous microcomposite of a silica network and highly fluorinated polymer having sulfonic acid groups.

4. The process of claim 1 comprising decomposing a compound of the formula Ar—C(CH$_3$)$_2$O$_2$H, wherein Ar is a substituted or unsubstituted mononuclear or polynuclear aromatic group.

5. The process of claim 1 wherein at least about 20 weight % of said particles of said catalyst have a size less than about 100 μm.

6. The process of claim 1 wherein said compound to be decomposed is selected from the group consisting of cumene hydroperoxide and diisopropylbenzene dihydroperoxide.

7. The process of claim 6 wherein said process is carried out in an organic solvent.

8. The process of claim 7 wherein said process is carried out in a solvent comprising acetone.

9. The process of claim 1 carried out at a temperature of about −15° C. to about 150° C.

10. The process of claim 1 carried out at temperature of about 20° C. to about 100° C.

11. A process for the manufacture of bisphenol A comprising:
  (a) decomposing cumene hydroperoxide in the presence of a catalyst containing highly fluorinated polymer having sulfonic acid groups to form a decomposition product mixture containing phenol and acetone; and
  (b) reacting said phenol and acetone of said decomposition product mixture in the presence of catalyst containing highly fluorinated polymer having sulfonic acid groups under conditions which form bisphenol A.

12. The process of claim 11 wherein at least a portion of said phenol and acetone of said decomposition product mixture is not separated from said catalyst prior to said reaction to form bisphenol A and the catalyst used for said decomposition is the same catalyst that is used for said reaction to bisphenol A.

13. The process of claim 11 wherein the mole ratio of phenol to acetone is increased prior to reaction to form bisphenol A.

14. The process of claim 13 wherein said mole ratio is increased by removing acetone from said decomposition product mixture.

15. The process of claim 11 wherein said catalyst is selected from the group consisting of (a) particles of highly fluorinated polymer having sulfonic acid groups and (b) particles of porous microcomposite of a metal oxide network and highly fluorinated polymer having sulfonic acid groups.

16. The process of claim 11 wherein said catalyst present during said decomposition of cumene hydroperoxide is in the form of a particles wherein at least about 20 weight % of said particles have a particle size of less than about 300 μm.

* * * * *